(12) United States Patent
Park

(10) Patent No.: US 6,514,132 B2
(45) Date of Patent: Feb. 4, 2003

(54) HARDENED SKIN CARE INSTRUMENT

(75) Inventor: Il-Yong Park, Seoul (KR)

(73) Assignee: Shinwoo Union Co., Ltd., Seoul (KR)

(*) Notice: Subject to any disclaimer, the term of this patent is extended or adjusted under 35 U.S.C. 154(b) by 0 days.

(21) Appl. No.: 09/922,793

(22) Filed: Aug. 7, 2001

(65) Prior Publication Data

US 2002/0193061 A1 Dec. 19, 2002

(30) Foreign Application Priority Data

Jun. 16, 2001 (KR) .......................................... 01-018055

(51) Int. Cl.$^7$ .............................. B24D 11/00; B24B 7/00
(52) U.S. Cl. .................... 451/527; 451/528; 451/557; 451/533; 451/534; 451/539
(58) Field of Search ................................. 451/527, 528, 451/530, 533, 539, 534; 132/76.4, 76.5; 407/29.1, 29.14, 29.15

(56) References Cited

U.S. PATENT DOCUMENTS

| 1,335,777 A | 4/1920 | Zelaya ........................ 132/76.4 |
| 2,557,175 A | 6/1951 | Cortes ........................ 132/76.4 |
| 2,597,525 A | 5/1952 | Kessler ....................... 132/75.8 |
| D186,752 S | 11/1959 | Dean .............................. 30/26 |
| 3,151,333 A | 10/1964 | Scholz .......................... 15/227 |
| 3,468,079 A | 9/1969 | Kaufman ................... 407/29.13 |
| 3,809,101 A | 5/1974 | Shimizu ..................... 132/76.4 |
| 4,047,902 A | 9/1977 | Wiand .......................... 451/548 |
| 4,397,325 A | 8/1983 | Van Roeyan .............. 132/75.6 |
| 5,357,717 A | 10/1994 | Friel et al. .................. 451/494 |
| 6,450,175 B1 | 9/2002 | Park .......................... 132/73.5 |

FOREIGN PATENT DOCUMENTS

| DE | WO 97/48306 | 12/1997 | .......... A45D/29/05 |
| KR | 0002806 | 5/1992 | |
| KR | 0005662 | 6/1997 | |
| KR | 0184656 | 3/2000 | |

*Primary Examiner*—M. Rachuba
(74) *Attorney, Agent, or Firm*—Greenblum & Bernstein, P.L.C.

(57) ABSTRACT

A hardened skin care instrument having a file tooth portion formed by an electroplating process is disclosed. The instrument including a handle part with a recessed portion formed thereon, and a head part comprises an abrasive piece attached to the head part. The abrasive piece includes a plurality of release grooves that are produced by corroding a selected portion of a copper film laid on one surface of a base made of synthetic resin, and a plurality of file tooth portions that are formed by adhering abrasive powder to the remaining portion of the copper film by an electroplating. The release grooves and file tooth portions are arranged to cross over each other.

3 Claims, 3 Drawing Sheets

[Fig. 1]
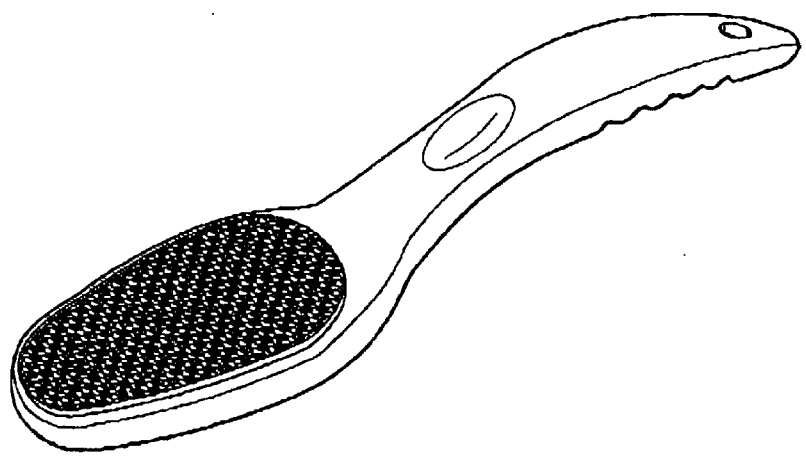
[Fig. 2]
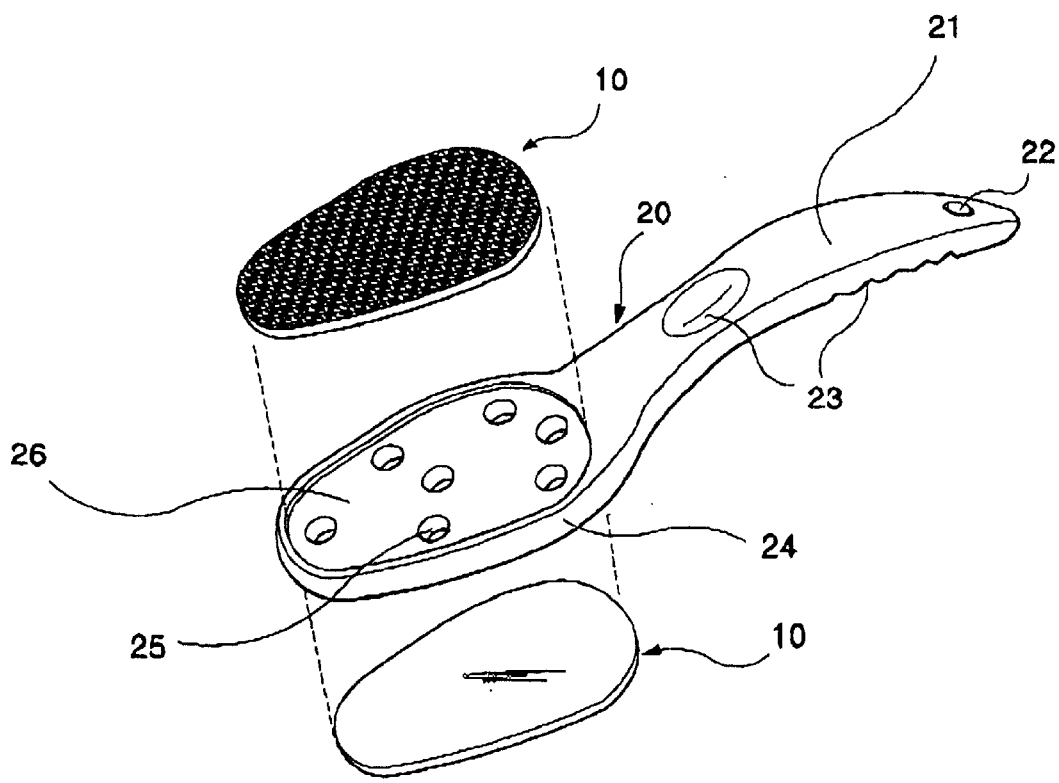

[Fig. 3]
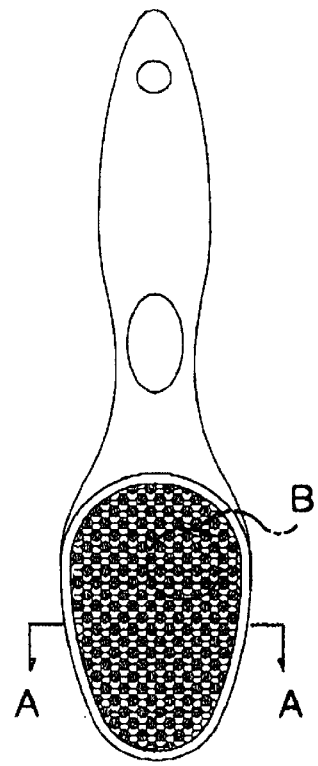
[Fig. 4]
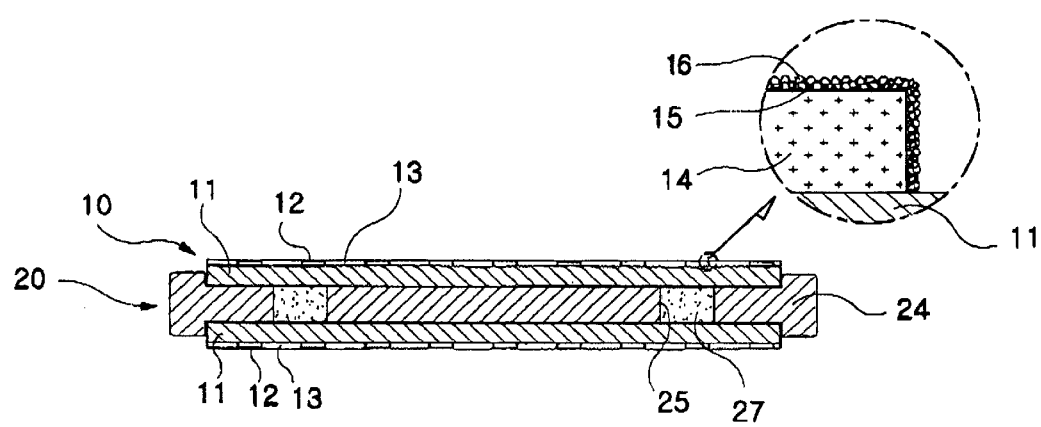

[Fig. 5]
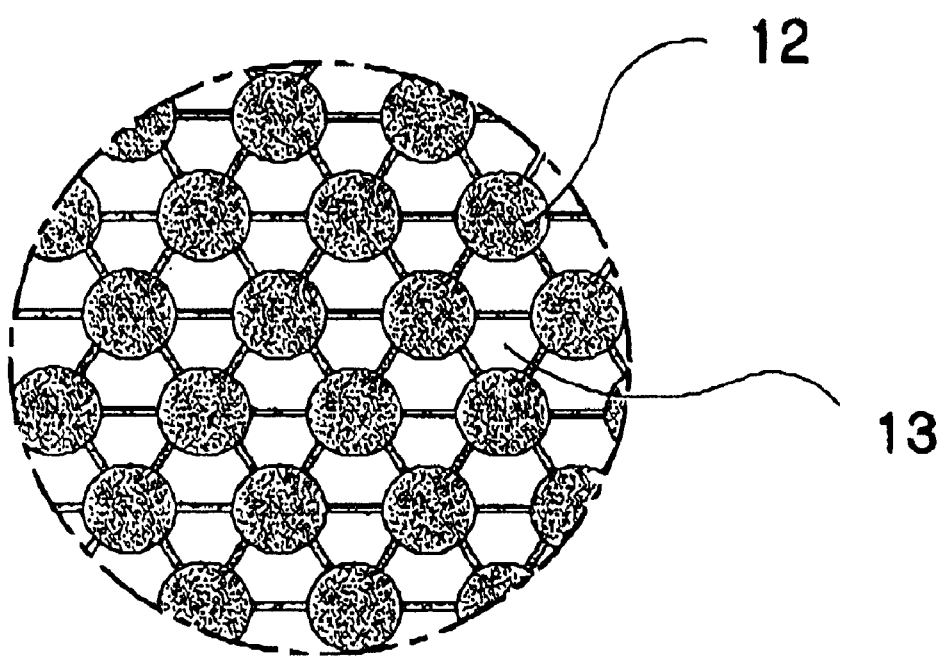

HARDENED SKIN CARE INSTRUMENT

BACKGROUND OF THE INVENTION

1. Field of the Invention

The present invention relates to a hardened skin care instrument, and more particularly, to a hardened skin care instrument having a file tooth portion formed by an electroplating process.

2. Background of the Related Art

A conventional hardened skin care instrument includes a grinding surface having a sandpaper (or a garnet paper) or stone powder adhered thereon using an adhesive. There are some problems as followings: since adhesive strength of the adhesive is gradually weakened due to the contact with moisture, the sandpaper or stone powder is detached from the grinding surface; and since filed substance lodges in grooves of the sandpaper or the stone powder, it is not easily cleaned by water.

In case that the grinding surface is made of porous pumice, since the hardness thereof is weak, if the pumice absorbs the moisture, the pumice is brittle. In addition, pores of the skin are filled with the powder of pumice, thereby injuring ones skin health.

Further, in case that a metal plate is punched to form a number of protruded portions which is being used as the grinding surface, since the protruded portions have a sharpened edge, a user is in danger of being injured.

Such hardened skin care instrument is disclosed in Publications of Korean Utility Model Registration Nos. 20-111062, 20-184656, and 20-067793, the hardened skin care instrument including the grinding surface with the sandpaper or stone powder adhered using the adhesive thereon. Since the abrasive powder is densely formed on the grinding surface, the filed substance lodges in the groove of the sandpaper or the stone powder. The filed substance is not easily removed from the groove. Therefore, there is much likelihood of the instrument getting moldy. In addition, there is a problem in that the adhesive strength of the adhesive is gradually weakened due to the frequent contact with the moisture. In particular, in case of adhering the sandpaper, there is another problem in that since a sheet with sands adhered thereon is made of a fabric or paper, if it is used in hot water for a long time, the sheet is detached from the grinding surface or the abrasive powder is released from the sheet.

SUMMARY OF THE INVENTION

Accordingly, the present invention is directed to a hardened skin care instrument that substantially obviates one or more problems due to limitations and disadvantages of the related art.

An object of the present invention is to provide a hardened skin care instrument, in which filed substance is effectively released from a file tooth portion, and the durability thereof is remarkably increased.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve the object and other advantages and in accordance with the purpose of the invention, as embodied and broadly described herein, in a hardened skin care instrument including a handle part with a recessed portion formed thereon, and a head part, the instrument comprises an abrasive piece attached to the head part, the abrasive including a plurality of release grooves that are produced by corroding a selected portion of a copper film laid on one surface of a base made of synthetic resin, and a plurality of file tooth portions that are formed by adhering abrasive powder to the remaining portion of the copper film by an electroplating, wherein the release grooves and file tooth portions are arranged to cross over each other.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 1 is a perspective view illustrating the assembled state of a hardened skin care instrument according to the present invention;

FIG. 2 is a perspective view illustrating the disassembled state of a hardened skin care instrument according to the present invention;

FIG. 3 is a top plan view illustrating the assembled state of a hardened skin care instrument according to the present invention;

FIG. 4 is an enlarged partial cross-sectional view taken along a line A—A in FIG. 3; and FIG. 5 is an enlarged top plan view of a circle indicated by the letter "B" in FIG. 3.

DETAILED DESCRIPTION OF THE PREFERRED EMBODIMENTS

Reference will now be made in detail to the preferred embodiment of the present invention, examples of which are illustrated in the accompanying drawings.

Referring to FIG. 2, a hardened skin care instrument of the present invention comprises abrasive pieces 10, with a file tooth portion 12 and a release groove 13 formed through a corrosion and plating process, and a body 20 with a handle part 21 and a head part 24 integrally formed with the handle part through an injection molding. The abrasive pieces are attached to a seating groove 26 of an upper and lower surface of the head part 24, respectively. Roughness of each abrasive piece is different to each other. The seating groove 26 is provided with several through holes 25, so that an adhesive 27 is filled in the through holes to rigidly hold the abrasive pieces 10. The handle part 21 is bent to allow the user to conveniently grip it. In order to prevent the slippage when gripping the handle part, a desired portion of the handle part is provided with a recessed portion 23. The handle part is also provided on an end thereof with a hang-up portion 22, so that the instrument may be hung on a hanger.

A major feature of the hardened skin care instrument according to the present invention is to manufacture the abrasive piece 10, in which the physical property of the abrasive piece is not changed under a hot and humid atmosphere, thereby maintaining the state of the instrument in an optimal condition. To achieve the feature, the release groove 13 and the file tooth portion 12 have to be arranged at a certain size and spacing, and the abrasive to be adhered to the abrasive portion 12 by an electroplating process has to have a proper grain size. In addition, the electroplating is achieved by using plating material having a good corrosion resistance, such as nickel.

FIG. 4 is an enlarged cross sectional view taken along a line A—A of FIG. 3, and illustrates the state that the abrasive pieces 10 are attached to the upper and lower surface of the head part 24. A manufacturing process of the abrasive piece will now be explained in detail.

The abrasive piece 10 includes the file tooth portion 12, the release groove 13, and a base 11 made of synthetic resin. The forming process of the release groove 13 is similar to a typical etching procedure manufacturing an electric circuit board. A mask film having a variety of patterns corresponding to a desired pattern of the release groove formed on a surface of the abrasive piece 10 is manufactured. Photoresist solution is coated on a copper film 14 formed on one surface of the base made of synthetic resin. After that, the mask film is aligned over the photoresist solution and the photoresist solution is then exposed to a light. The exposed portions of the photoresist solution coated on the copper film is hardened. Non-exposed portions are removed on the copper film. Afterwards, the resultant base is dipped in a corrosive solution and thus the exposed portions of the copper film 14 which is not covered with the photoresist pattern is removed, thereby forming a number of release grooves 13.

The file tooth portions will be formed on the non-corroded portions of the copper film. The file tooth portion may have various shapes such as a circle, a hexagon, a band or the like. These shapes are manufactured in such a manner that the file tooth portions are connected to each other, so that an electric current flows through the file tooth portions in course of the electroplating as described below.

Next, a forming process of the file tooth portion 12 will now be explained. After the hardened photoresist solution existed on the copper film 14 is dissolved using an alkaline solution such as caustic soda, the copper film 14 connected to the cathode is immersed into a nickel plating solution. The nickel plating solution is in a state mixed with white alumina powder 16. When electroplating the nickel and the alumina powder on the copper film, the nickel is plated on the surface of the copper film 14 to form a nickel film 15, and the white alumina powder 16 is rigidly attached to the surface of the copper film 14.

Again explaining the above process with reference to FIG. 4, the release groove 13 is formed on a portion of the abrasive piece 10 by the corrosion, while the white alumina powder is attached to other portion of the abrasive piece by the electroplating to form the file tooth portion 12. FIG. 4 illustrates the surface of the file tooth portion 12, in which alumina powder 16 is uniformly adhered to the nickel film 15 plated on the surface.

Particles of the alumina power 16 adhered to the file tooth portion 12 have a certain grain size suitable for use in cutting or grinding of calluses or hardened skin. Preferably, an abrasive having a large grain size to be rigidly adhered to the file tooth portion in course of the electroplating may be used. The used white alumina powder 16 is only one example of the present invention, while other abrasive having a corrosion resistance and a sufficient abrasive strength can be used. Also, the used nickel plating solution is only one example of the present invention, while various metal plating solution having a corrosion resistance may be used.

FIG. 5 is an enlarged top plan view of a circle indicated by the letter "B" in FIG. 3, in which the release groove 13 and the file tooth portion 12 of the abrasive piece 10 are shown. Each of the file tooth portions 12 has a circular shape, and six file tooth portions 12 are arranged in a hexagonal shape around one file tooth portion. The circular file tooth portions 12 are connected through a line, so that the electrical current flows to the file tooth portions through the line. The remaining portion of the abrasive piece forms the release groove 13 as described above.

In order to maximize the release of the filed substance (filed powder of the hardened skin), the region of the release groove 13 is sufficiently allocated to cross over the file tooth portion in a proper width and spacing, thereby increasing the filling effect. The filed substance produced from the filing is gathered in the release groove 13. The file tooth portions 12 and release grooves 13 are arranged to have a width and spacing sufficient to remove the hardened skin.

Although the pattern shown in FIG. 5 is one example of the present invention, other shape of pattern may be formed by changing the arrangement of the release groove and file tooth portion.

The abrasive pieces 10 with a grinding surface having different roughness are attached to the seating grooves 26 of the upper and lower surface of the head part 24, respectively. The user scrubs the hardened skin of elbows, knees and heels using the handle part 21 of the instrument to grind the hardened skin.

According to the construction, the hardened skin is ground with the file tooth portion 12 with the white alumina powder 16 adhered thereto, and the filed substance produced during the filing is easily released from the release groove 13. In addition, since the filed substance does not lodge in the release groove, this is a sanitary hardened skin care instrument of the present invention, relative to the prior art in which the file tooth portion is formed on the entire surface. Moreover, the abrasive is rigidly attached by using the electroplating. Further, since the metal plating using the plating material having the corrosion resistance is used, although the abrasive is exposed to the moisture for a long time, the physical property of the abrasive is not changed, thereby extending the durability thereof.

The forgoing embodiment is merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A hardened skin care instrument including a handle part with a recessed portion formed thereon, and a head part, the instrument comprising:

an abrasive piece attached to the head part, the abrasive piece including a plurality of release grooves that are produced by corroding a selected portion of a copper film laid on one surface of a base made of synthetic resin, and a plurality of file tooth portions that are formed by adhering abrasive powder to the remaining portion of the copper film by an electroplating, wherein the release grooves and file tooth portions are arranged to cross over each other.

2. The instrument as claimed in claim 1, wherein the abrasive powder is white alumina.

3. The instrument as claimed in claim 1, wherein the head part has a seating groove with a through hole formed thereon.

* * * * *